United States Patent [19]
Rohrbach et al.

[11] 3,987,170
[45] Oct. 19, 1976

[54] WATER-SOLUBLE SALTS OF PARACETAMOL
[75] Inventors: Philippe Rohrbach, Paris; Claude Rissé, Saint-Michel-sur-Orge; Jean-Charles Jinot, Paris, all of France
[73] Assignee: Societe Bottu, Paris, France
[22] Filed: June 24, 1975
[21] Appl. No.: 589,894

[52] U.S. Cl. ............................. 424/250; 260/268 R
[51] Int. Cl.² ............... A61K 31/495; C07D 295/00
[58] Field of Search ................. 260/268 R; 424/250

[56] References Cited
OTHER PUBLICATIONS
Chow et al. – Chem. Abst., vol. 77, (1972), p. 130,534C.

Primary Examiner—Sam Rosen
Attorney, Agent, or Firm—Lewis H. Eslinger

[57] ABSTRACT
Hydrosoluble salts of paracetamol with an amine, in particular with a piperazine represented by the formula:-

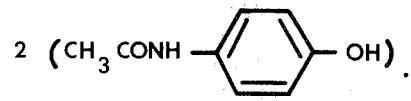

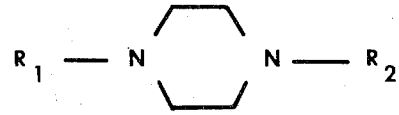

(in which $R_1$ and $R_2$, which may be the same or different, are each a hydrogen atom or a lower alkyl group), and pharmaceutical compositions containing at least one of these salts as active ingredient in association with a physiologically acceptable aqueous medium, for example in orally administrable forms, such as effervescent compounds, soluble powders, syrups, or in parenterally administrable forms, such as injectable solutions, making it possible to administer high doses of paracetamol in aqueous solution.

8 Claims, No Drawings

WATER-SOLUBLE SALTS OF PARACETAMOL

This invention relates to paracetamol derivatives possessing analgesic and antipyretic activity.

Paracetamol is sparingly soluble in water (approximately 1.3g per 100 ml), and such solutions have a very unpleasant taste. The usual route of administration is therefore using a solid oral form, to be swallowed, generally in tablet form. However, active substances act more quickly if previously solubilized, and certain patients are unable, or unwilling, to swallow tablets.

Attempts have been made hitherto at presenting paracetamol in the form of effervescent tablets. A relatively low dose results (0.30g generally), with a rather slow release of carbon dioxide (2 minutes, for example) and a final excess of alkali (bicarbonate, for example), but it is possible to solubilize the active principle. However, such a form, in addition to the too low posology and rather slow crumbling, has a very unpleasant taste whatever sweetener is used.

Liquid forms have also been proposed hitherto, using a "suspension" or solution obtained by dissolving a desired amount of paracetamol and using a certain proportion of a non-aqueous solvent.

In the case of suspensions, there is the risk of non-homogeneity which is minimised by making the solutions too viscous, while suspending agents tend to introduce more or less unpleasant flavors.

In the case of solutions, the solubilizing solvent is generally alcohol, but it can for example, be glycerol, or glycols, which are used in proportions ranging from 7 to 25%. Such proportions give the solutions a burning taste, and the solvents are not without harmful effects, making the resulting preparations contraindicated or limited in application, in particular with children.

It has also been proposed to form the sodium phenate of paracetamol, which has increased solubility, but aqueous solutions of this derivative are unfortunately very alkaline.

According to the present invention there are provided salts of paracetamol with an organic base.

Organic bases, and in particular amines, such as piperazine, form stable, water-soluble salts with paracetamol. Using aqueous solutions of these salts, it is possible to obtain adequate paracetamol concentrations for administration. Such solutions can easily be sweetened, and this avoids many of the disadvantages of hitherto proposed pharmaceutical forms of paracetamol.

Piperazine salts of paracetamol which are preferred are represented by the formula:

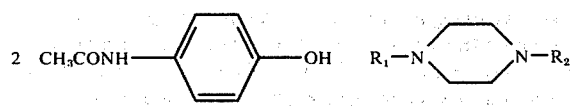

2 CH$_3$CONH—⟨C$_6$H$_4$⟩—OH    R$_1$—N⟨ ⟩N—R$_2$ (wherein R$_1$ and R$_2$, which can be the same or different, each represent a hydrogen atom or a lower alkyl group).

Soluble paracetamol salts in accordance with the invention can be prepared by reacting a solution of paracetamol in a solvent, such as isopropanol, with a solution of a stoichiometric amount of a particular amine in the same solvent, with heating until a clear solution is obtained. The reaction mixture can be worked up by allowing it to cool, after which it is refrigerated. The precipitate obtained can be filtered off, washed with the reaction mixture, then with ether, and dried.

The following Examples are given by way of illustration only, and they illustrate the preparation of paracetamol salts of piperazine and of N,N'-dimethyl-piperazine.

EXAMPLE 1

Preparation of the piperazine salt of paracetamol:

5g ($3.3 \times 10^{-2}$ moles) of paracetamol were dissolved in 25 ml of warm isopropanol. A solution of 1.72 g ($2 \times 10^{-2}$ moles) of piperazine in 8.75 ml of isopropanol was then added, and the mixture was heated until a clear solution was obtained. Thereafter it was allowed to cool, and this solution was refrigerated. The precipitate obtained was filtered off, washed with isopropanol, then with ether, and it was dried. 5.55 g of a white crystalline product were obtained (yield: 86.5%). Elemental analysis corresponded to the formula $2C_8H_9O_2N \cdot C_4H_{10}N_2$. The product melted sharply at 149° C (capillary tube).

The IR spectrum (KRr disc) of this derivative was different from the spectra of the starting materials, particularly in the presence of a wide band at about 2550 cm$^{-1}$, attributable to $=\overset{+}{N}H_2$ and characteristic of salt-formation. Moreover, the —OH band situated at about 3160 cm$^{-1}$ had disappeared, and the amde II band had shifted from 1565 to 1530 cm$^{-1}$.

The piperazine salt of paracetamol was stable at ambient temperature. It was instantaneously soluble in water at the rate of 2.6 g per 100 ml (equivalent to 2 g of paracetamol per 100 ml). The solution was stable and had a pH of 9.5.

EXAMPLE 2

Preparation of the N,N'-dimethylpiperazine salt of paracetamol

In a manner similar to that described in Example 1, 10 g of paracetamol were dissolved with slight heating in 50 ml of isopropanol, and a solution of N,N'-dimethylpiperazine in 20 ml of isopropanol was added. The solution obtained was cooled. After refrigeration and filtration, the product was rinsed with ether. After drying, 11.68 g of a white crystalline product were obtained (yield 85%). The product melted at 163° C. Elemental analysis corresponded to the formula $2C_8H_9NO_2 \cdot C_6H_{14}N_2$.

This salt was stable at room temperature. It was soluble in water at the rate of 2.75 g per 100 ml (equivalent to 2 g of paracetamol per 100 ml). This solution had a pH of 8.7.

The piperazine salt of paracetamol was subjected to pharmacological tests, the results of which are given hereinafter.

1. Analgesic Test according to R. KOSTER et al. (*Fed.Proc.* 1959, 18, 412) consisted of intraperitoneally injecting 0.5 ml of acetic acid in mice at the rate of 0.5 g per 100 cm$^3$, and counting the number of contorsions in the following 10 minutes. The analgesic effect of paracetamol or its salt administered orally 1 hour before this injection was revealed by the percentage decrease in the number of contorsions in relation to the controls:

| | dose per kilo | | percentage activity |
|---|---|---|---|
| | millimole | mg | |
| paracetamol | ½ | 75.5 | 78 |
| piperazine salt of paracetamol | ¼ | 97 | 81 |

2. Antipyretic Test according to WINDER et al. (*J. of Pharmac. and exp. Ther.* 1961, 133, 117) consisted of following the increase in temperature of control and treated rats, every hour for 5 hours, after the subcutaneous administration of a pyretogenic agent (based on brewers' yeast):

| | Increase of temperature after (hrs): | | | | |
|---|---|---|---|---|---|
| | 1 | 2 | 3 | 4 | 5 |
| Pyrexia control | 0.9 | 1.1 | 0.7 | 0.9 | 0.8 |
| Paracetamol ½mole or 75.5 mg/kg | 0 | −0.2 | 0.5 | 0.9 | 1.2 |
| Piperazine salt of paracetamol ¼ mole or 97 mg/kg | −0.1 | 0.1 | 0.6 | 1.0 | 1.0 |

These results show that the piperazine salt of paracetamol had qualitatively and quantitatively the properties of paracetamol, its action being moreover a function of its water-solubility and of the effects of piperazine itself.

The effectiveness of the piperazine salt of paracetamol as an analgesic-antipyretic was verified in man. A dose of 0.20 g to 2.6 g per administration was used, i.e. 0.40 to 7.8 g per 24 hours.

The solubility in water of paracetamol salts in accordance with the invention enables them to be used in preparations for oral administration, such as effervescent tablets, soluble powder sachets, syrups, injectable aqueous solutions, and the unit dose of the salt can be decidedly higher than if paracetamol itself were used.

The following are Examples of compositions in accordance with the invention:

EXAMPLE 3

Effervescent Tablet: For a tablet of approximately 3.600 g.

| | |
|---|---|
| Piperazine salt of paracetamol | 0.65 g |
| Sodium bicarbonate | 1.35 g |
| Anhydrous citric acid | 1.23 g |
| Glycocoll | 0.30 g |
| Sodium benzoate | 0.08 g |
| Sweetener (sodium saccharinate and flavour) | q.s. |

The paracetamol salt, the sodium bicarbonate, the anhydrous citric acid, and half the given amounts of glycocoll and sodium benzoate were mixed, and the mixture was compacted. After crushing and sifting, the granulate obtained was mixed with the sweetener and the remainder of the glycocoll and sodium benzoate, and then compressed to the desired weight.

An effervescent tablet was thus obtained having a sufficient dose of paracetamol (0.50 g).

EXAMPLE 4

Syrup

| | |
|---|---|
| Piperazine salt of paracetamol | 3.0 g |
| Distilled Water | 20.0 g |
| Polyethylene-glycol (M.P. 4000) | 2.5 g |
| Sodium Methyl Parahydroxybenzoate | 0.15 g |
| Citric Acid and Sweetener | q.s. |
| Sugar syrup | q.s.p. 100 g |

The sodium methyl parahydroxybenzoate and the polyethylene glycol were dissolved in the distilled water. The greater part of the sugar syrup was added, and the piperazine salt of paracetamol was dissolved in this medium with slight heating. The citric acid and the sweetener were added, and the desired weight was made up with sugar syrup.

In this formulation, the paracetamol was present in solution in an amount greater than that with hitherto proposed alcoholized syrups, and it could be very pleasantly sweetened.

EXAMPLE 5

Injectable Water Solution

| | | |
|---|---|---|
| Piperazine salt of paracetamol in the form of a lyophilized powder | | 0.26 g |
| Sodium chloride | q.s. | isotonic |
| Water for injectable preparation | | 10 ml |

The piperazine salt of paracetamol, in the form of a lyophilized powder, was obtained by lyophilization of a sterile solution of the active principle in water. The solubility of the product and the pH of the solution were compatible with the pH of the human body, and enabled paracetamol to be administered parenterally.

EXAMPLE 6

Soluble Sachet

| | |
|---|---|
| Piperazine salt of paracetamol | 1.285 g |
| Trisodium Citrate | 0.50 g |
| Anhydrous citric acid | 0.55 g |
| Sodium saccharinate | 0.02 g |
| Colouring Matter | q.s. |
| Flavouring | q.s. |
| Sugar | q.s.p. one 8 g sachet |

The various components were mixed, as required, after crushing in the event of different grain sizes.

Due to the use of the piperazine salt of paracetamol the soluble sachet form enabled an active dose of paracetamol (1g) to be administered in solution as a product with a very pleasant taste.

We claim:

1. A water-soluble salt of paracetamol of the formula:

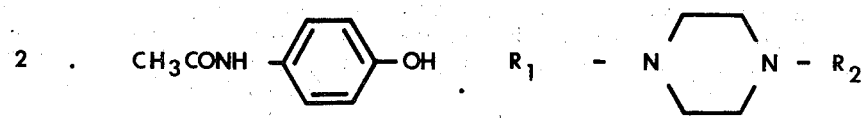

wherein $R_1$ and $R_2$, which may be the same or different, each is hydrogen or lower alkyl.

2. A salt according to claim 1, wherein $R_1$ and $R_2$ both are hydrogen.

3. A salt according to claim 1, wherein $R_1$ and $R_2$ are both methyl.

4. A pharmaceutical composition comprising an effective amount of a salt according to claim 1 as active ingredient, in association with a physiologically acceptable carrier.

5. A pharmaceutical composition comprising an effective amount of a salt according to claim 1 as active ingredient, in association with a physiologically acceptable aqueous medium.

6. A composition according to claim 4, in an orally administrable form, as an effervescent tablet, a sachet of water-soluble powder, or a syrup, the unit dose being 0.20 to 2.6 g of active ingredient.

7. A composition according to claim 5, in a parenterally administrable form, the dose of active ingredient per ampoule being 0.20 to 2.6 g.

8. A method of treatment of a disease accompanied by pain and fever, which comprises administering a composition according to claim 5 at a dose of 0.40 to 7.8 g of active ingredient per 24 hours.

* * * * *